(12) United States Patent
Koester et al.

(10) Patent No.: US 6,656,454 B1
(45) Date of Patent: Dec. 2, 2003

(54) METHOD FOR PRODUCING SURFACTANT GRANULATES

(75) Inventors: Josef Koester, Duesseldorf (DE); Werner Seipel, Hilden (DE); Celia Kosboth, Duisburg (DE); Hermann Hensen, Haan (DE); Anke Eggers, Duesseldorf (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 09/936,376

(22) PCT Filed: Mar. 3, 2000

(86) PCT No.: PCT/EP00/01836

§ 371 (c)(1),
(2), (4) Date: Dec. 20, 2001

(87) PCT Pub. No.: WO00/55293

PCT Pub. Date: Sep. 21, 2000

(30) Foreign Application Priority Data

Mar. 12, 1999 (DE) .......................... 199 11 040

(51) Int. Cl.$^7$ .................................. A61K 7/16
(52) U.S. Cl. .......................... 424/49; 424/56
(58) Field of Search ................ 424/49–58

(56) References Cited

U.S. PATENT DOCUMENTS

| | | | |
|---|---|---|---|
| 4,765,976 A | | 8/1988 | Grollier et al. |
| 5,189,207 A | | 2/1993 | Blasey et al. |
| 5,312,932 A | | 5/1994 | Behler et al. |
| 5,322,957 A | | 6/1994 | Fabry et al. |
| 5,397,507 A | * | 3/1995 | Bauer et al. ............... 252/548 |
| 5,484,531 A | | 1/1996 | Kuehne et al. |
| 5,516,447 A | * | 5/1996 | Bauer et al. ............... 252/89.1 |
| 5,519,948 A | * | 5/1996 | Raehse et al. ............. 34/347 |
| 5,597,794 A | * | 1/1997 | Bauer et al. ............... 510/457 |
| 5,629,275 A | * | 5/1997 | Bauer et al. ............... 510/108 |
| 5,739,097 A | * | 4/1998 | Bauer et al. ............... 510/446 |
| 5,866,530 A | * | 2/1999 | Schmid et al. ............. 510/438 |
| 5,962,663 A | | 10/1999 | Wachter et al. |
| 6,030,937 A | * | 2/2000 | Kruse et al. ............... 510/443 |
| 6,140,302 A | * | 10/2000 | Lueder et al. ............. 510/444 |
| 6,191,097 B1 | * | 2/2001 | Lueder et al. ............. 510/444 |
| 6,288,021 B1 | * | 9/2001 | Lueder et al. ............. 510/445 |
| 6,340,665 B1 | * | 1/2002 | Lueder et al. ............. 510/470 |
| 6,362,157 B1 | * | 3/2002 | Blochwitz et al. ......... 510/444 |
| 6,455,488 B1 | * | 9/2002 | Assmann et al. .......... 510/445 |

FOREIGN PATENT DOCUMENTS

| | | |
|---|---|---|
| CA | 2101079 | 8/1994 |
| DE | 41 27 323 A1 | 2/1993 |
| DE | 42 04 700 A1 | 8/1993 |
| DE | 43 03 176 A1 | 8/1994 |
| DE | 43 03 211 A1 | 8/1994 |
| DE | 37 13 099 C2 | 2/1996 |
| DE | 44 42 987 A1 | 6/1996 |
| DE | 195 37 001 A1 | 3/1997 |
| DE | 196 04 180 A1 | 8/1997 |
| DE | 196 41 275 C1 | 3/1998 |
| DE | 298 21 774 U1 | 4/1999 |
| EP | 0 319 819 A1 | 6/1989 |
| EP | 0 561 825 B1 | 9/1995 |
| EP | 0 561 999 B1 | 1/1996 |
| FR | 2 701 266 A1 | 8/1994 |

OTHER PUBLICATIONS

Biswas, et al., "Surface–Active Properties of Sodium Salts of Sulfated Fatty Acid Monoglycerides", The Journal Of The American Oil Chemists' Society, vol. 37, (Apr., 1960), pp. 171–175.

Ahmed, "Efficient Synthesis of Fatty Monoglyceride Sulfates from Fatty Acids and Fatty Acid Methyl Esters", JAOCS, vol. 67, No. 1, (Jan., 1990) pp. 8–14.

Schoenberg, "Sulfosuccinate Surfactants—Mildness and Low Cost have Spurred Growth in Body, Hair, and Skin Cleansers", Cosmetics & Toiletries, vol. 104, (Nov., 1989), pp. 105–106, 108–110 & 112.

Milne, "Trends in the Applications for Sulphosuccinate Surfactants", R. Soc. Chem, (Ind. Appl. Surf. II), vol. 77, (1990), pp. 76–100.

Hreczuch, et al., "Effect of Narrowing Oxirane Adduct Distribution on Some Properties of Ethoxylated Alcohol–Based Sulfosuccinic Acid Halfesters", JAOCS., vol. 70, No. 7, (Jul., 1993), pp. 707–710.

Biermann, et al., "Alkylpolyglucoside—Technologie und Eigenschaften", Starch/Stärke, vol. 45, VCH Verlagsgesellschaft mbH, Weinheim, (1993), pp. 281–288, p. 6 line 11–14.

Salka, "Alkyl Polyglycosides Properties and Applications", Cosmetics & Toiletries, vol. 108, (Mar., 1993), pp. 89–94.

Kahre, et al, "Alkylpolyglycoside—Ein neues Konzept für Pflege und Verträglichkeit in der Kosmetik", SÖFW–Journal, vol. 121, No. 8, (1995), pp. 598, 600–601, 604–611, p. 6 lines 11–14.

Tuvell, et al., "AOS—An Anionic Surfactant System: Its Manufacture, Composition, Properties, and Potential Application", J. Am. Oil Chemist' Soc., vol. 55, (Jan., 1978), pp. 70–80.

(List continued on next page.)

*Primary Examiner*—Shep K. Rose

(57) ABSTRACT

Aqueous oral and dental care compositions are comprising of: (a) from about 0.1 to about 20% by weight of surfactant granules which are the product of the process which comprises subjecting an aqueous paste comprised of from about 40 to about 60% by weight of a monoglyceride (ether) sulfate to simultaneous drying and granulation in a fluidized bed; (b) from about 1 to about 25% by weight of an abrasive, a polish, or a combination thereof; (c) from 0 to about 65% by weight of a humectant; (d) from 0 to about 2% by weight of chitosan; (e) from 0 to about 3% by weight of a flavoring and; (f) from 0 to about 5% by weight other auxiliaries including water wherein the weight of all components adds up to 100% by weight.

6 Claims, No Drawings

OTHER PUBLICATIONS

"Ullmann's Encyclopedia of Industrial Chemistry", Weinheim, Verlag Chemie, 5$^{th}$ Ed., vol. A6, (1986), pp. 231–332.

Gesslein, et al., "Chitosan—a Gift from the Sea", HAPPI, vol. 27, (Oct., 1990), pp. 57 & 59.

Skaugrud, "Chitosan—New Biopolymer for Cosmetics & Drugs", Drug Cosm. Ind., vol. 148, (May, 1991), pp. 24, 26 & 30.

Onsøyen, et al., "Adding Benefits to Cosmetic Formulations by Tailormade Chitosans", Seifen–Öle–Fette–Wachse, vol. 117, (1991), pp. 633–637.

Sannan, et al., "Effect of Deacetylation on Solubility", Makromol. Chem., vol. 177, (1976), pp. 3589–3600.

Von Wilmsmann, "Schaumbestimmung von Tensiden mit einer Reibschaummethode", Fette–Seifen–Anstrichmittel, vol. 66, No. 11, (1964), pp. 955–961.

* cited by examiner

METHOD FOR PRODUCING SURFACTANT GRANULATES

BACKGROUND OF THE INVENTION

This invention relates to the use of special surfactant granules for the production of surface-active compositions, preferably detergents, soaps and oral and dental care preparations.

1. Prior Art

Monoglyceride (ether) sulfates are acquiring increasing significance for use in surface-active compositions by virtue of their excellent detersive properties. Hitherto, they have generally been used in the form of water-containing preparations. A major disadvantage of this is that these pastes generally contain between 50 and 75% by weight of water in order to be sufficiently pumpable. On the market, however, there is a heavy demand for solid water-free supply forms which can be incorporated in particular in powder-form detergents, tooth creams or syndet soaps without having to be dried beforehand.

Solid monoglyceride (ether) sulfates obtained, for example, by drying and simultaneous granulation in a thin layer in a so-called flash dryer are known from the prior art (DE 19641275 C1). Unfortunately, the surfactants produced in this way have unsatisfactory dissolving properties in detergents.

Accordingly, the problem addressed by the present invention was to provide a solid supply form of monoglyceride (ether) sulfates which could be prepared with a little water and which would be distinguished by improved dissolving behaviour in laundry detergents, dishwashing detergents and cleaning compositions.

2. Description of the Invention

The present invention relates to surfactant granules obtainable by subjecting 20 to 60% by weight and preferably 40 to 50% by weight aqueous pastes containing monoglyceride (ether) sulfates to simultaneous drying and granulation in a fluidized bed.

The present invention also relates to the use of these surfactant granules for the production of surface-active compositions, preferably oral and dental care preparations.

It has surprisingly been found that the drying and granulation of aqueous surfactant pastes in a fluidized bed ("SKET granulation") leads to solid supply forms of the monoglyceride (ether)sulfate which are distinguished by excellent dissolving behavior in laundry detergents, dishwashing detergents and cleaning compositions. In addition, monoglyceride (ether) sulfate granules produced in this way have an abrasive effect in oral and dental care preparations and may therefore be used as a substitute for other abrasives. This has the particular advantage that the quantity of abrasives can be reduced without any effect on abrasive performance. Bar soaps containing monoglyceride (ether) sulfate granules as surfactant component are distinguished by good foaming behavior, better stability in air and a reduced tendency towards softening.

In combination with other surfactants, especially fatty alcohol sulfates, sulfosuccinates, olefin sulfonates, alkyl and/or alkenyl oligoglycosides, a synergistic improvement in the properties mentioned is observed. In addition, where these granules are used in the described compositions, there is no need for the removal of water which would be necessary if comparable aqueous pastes were used.

Monoglyceride (Ether) Sulfates

Monoglyceride sulfates and monoglyceride ether sulfates are known anionic surfactants which may be obtained by the relevant methods of preparative organic chemistry. They are normally produced from triglycerides which, optionally after ethoxylation, are transesterified to the monoglycerides and then sulfated and neutralized. The partial glycerides can also be reacted with suitable sulfating agents, preferably gaseous sulfur trioxide or chlorosulfonic acid [cf. EP 0 561 825 B1, EP 0 561 999 B1 (Henkel)]. If desired, the neutralized products may be subjected to ultrafiltration to reduce their electrolyte content to the required level [DE 42 04 700 A1 (Henkel)]. Overviews of the chemistry of monoglyceride sulfates have been published, for example, by A. K. Biswas et al. In J. Am. Oil. Chem. Soc. 37, 171 (1960) and F. Ahmed in J. Am. Oil. Chem. Soc. 67, 8 (1990). The monoglyceride (ether) sulfates suitable for use in accordance with the invention correspond to formula (I):

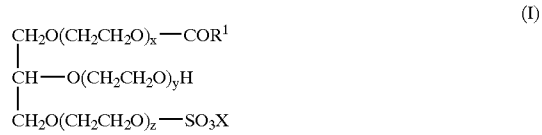

in which $R^1CO$ is a linear or branched acyl group containing 6 to 22 carbon atoms, x, y and z together stand for 0 or for numbers of 1 to 30, preferably 2 to 10, and X is an alkali metal or alkaline earth metal. Typical examples of monoglyceride (ether)sulfates suitable for the purposes of the invention are the reaction products of lauric acid monoglyceride, coconut fatty acid monoglyceride, palmitic acid monoglyceride, stearic acid monoglyceride, oleic acid monoglyceride and tallow fatty acid monoglyceride and ethylene oxide adducts thereof with sulfur trioxide or chlorosulfonic acid in the form of their sodium salts. Monoglyceride sulfates corresponding to formula (I) in which $R^1CO$ is a linear acyl group containing 8 to 18 carbon atoms and preferably 12 to 14 carbon atoms, x, y and z=0 and X is sodium are preferably used.

Surfactants/surfactant Granules

In one preferred embodiment of the invention, aqueous pastes containing fatty alcohol sulfates, sulfosuccinates, olefin sulfonates, alkyl and/or alkenyl oligoglycosides as further surfactants are dried and granulated. Alternatively, the monoglyceride (ether) sulfate granules may be present in admixture with granules of fatty alcohol sulfates, sulfosuccinates, olefin sulfonates, alkyl and/or alkenyl oligoglycosides such as, for example, monoglyceride (ether) sulfate, fatty alcohol sulfate, alkyl and/or alkenyl oligoglycoside granules.

Fatty Alcohol Sulfates

Fatty alcohol sulfates are understood to be primary aliphatic alkyl sulfates corresponding to formula (II):

in which $R^2$ is a linear or branched, saturated or unsaturated hydrocarbon radical containing 12 to 14 carbon atoms and X is an alkali metal and/or alkaline earth metal, ammonium, alkyl ammonium, alkanolammonium or glucammonium. Fatty alcohol sulfates are known anionic surfactants which are preferably obtained by sulfation of native fatty alcohols or synthetic oxoalcohols and subsequent neutralization. Typical examples of fatty alcohol sulfates are the sodium salts of sulfation products of lauryl alcohol, isotridecyl alcohol, myristyl alcohol and the technical mixtures thereof obtained, for example, in the high-pressure hydrogenation of technical methyl esters based on fats and oils or aldehydes from Roelen's oxo synthesis and as monomer fraction in the dimerization of unsaturated fatty alcohols. Fatty alcohols containing 12 to 14 carbon atoms such as, for example, technical $C_{12/14}$ coconut alcohol sulfates and, more particularly, lauryl alcohol are preferably used.

Sulfosuccinates

Sulfosuccinates, which are also referred to as sulfosuccinic acid esters, are known anionic surfactants which may be obtained by the relevant methods of preparative organic chemistry. They correspond to formula (III):

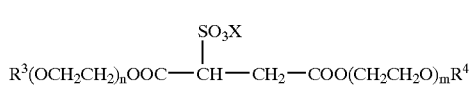

(III)

where $R^3$ is an alkyl and/or alkenyl group containing 6 to 22 carbon atoms, $R^4$ has the same meaning as $R^3$ or X, n and m independently of one another stand for 0 or for numbers of 1 to 10 and X is an alkali metal or alkaline earth metal, ammonium, alkylammonium, alkanolammonium or glucammonium. They are normally produced from maleic acid, but preferably from maleic anhydride, which in a first step is esterified with optionally ethoxylated primary alcohols. The monoester-to-diester ratio can be adjusted at this stage by varying the quantity of alcohol and the temperature. The second step comprises the addition of bisulfite which is normally carried out in methanol as solvent. Fairly recent overviews of the production and use of sulfosuccinates have been published, for example, by T. Schoenberg in Cosm. Toil. 104, 105 (1989), by J. A. Milne in R. Soc. Chem. (Ind. Appl. Surf. II) 77, 77 (1990) and by W. Hreczurch et al in J. Am. Oil. Chem. Soc. 70 707 (1993). Typical examples are sulfosuccinic acid monoesters and/or diesters in the form of their sodium salts which are derived from fatty alcohols containing 8 to 18 and preferably 8 to 10 or 12 to 14 carbon atoms. The fatty alcohols may be etherified with on average 1 to 10 and preferably 1 to 5 moles of ethylene oxide and may have both a conventional and—preferably—a narrow homolog distribution. Di-n-octyl sulfosuccinate and monolauryl-3EO-sulfosuccinate in the form of their sodium salts are mentioned as examples.

Alkyl and/or Alkenyl Oligoglycosides

Alkyl and/or alkenyl oligoglycosides are known nonionic surfactants which correspond to formula (IV):

$$R^5O\text{—}[G]_p \quad (IV)$$

where $R^5$ is an alkyl and/or alkenyl radical containing 4 to 22 carbon atoms, G is a sugar unit containing 5 or 6 carbon atoms and p is a number of 1 to 10. They may be obtained by the relevant methods of preparative organic chemistry. The synoptic articles by Biermann et al. in Starch/Stärke 45, 281 (1993), B. Salka in Cosm. Toil. 108, 89 (1993) and J. Kahre et al. in SÖFW-Journal No. 8, 598 (1995) are cited as representative of the extensive literature available on this subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (IV) indicates the degree of oligomerization (DP), i.e. the distribution of mono-and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view. The alkyl or alkenyl radical $R^5$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl radical $R^5$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ coconut oil fatty alcohol having a DP of 1 to 3 are preferred.

Olefin Sulfonates

The compositions according to the invention contain as a further constituent olefin sulfonates which are normally obtained by addition of $SO_3$ onto olefins corresponding to formula (V):

$$R^6\text{—}CH\text{=}CH\text{—}R^7 \quad (V)$$

in which $R^6$ and $R^7$ independently of one another represent H or alkyl groups containing 1 to 20 carbon atoms, with the proviso that $R^6$ and $R^7$ together contain at least 6 and preferably 10 to 16 carbon atoms, and subsequent hydrolysis and neutralization. Particulars of their production and use can be found in a synoptic article published in J. Am. Oil. Chem. Soc. 55, 70 (1978).

Internal olefin sulfonates may be used although α-olefin sulfonates which are obtained where $R^6$ or $R^7$ is hydrogen are preferably used. Typical examples of the olefin sulfonates used are the sulfonation products obtained by reacting $SO_3$ with 1-, 2-butene, 1-, 2-, 3-hexene, 1-, 2-, 3-, 4-octene, 1-, 2-, 3-, 4-, 5-decene, 1-, 2-, 3-, 4-, 5-, 6-dodecene, 1-, 2-, 3-, 4-, 5-, 6-, 7-tetradecene, 1-, 2-, 3-, 4-, 5-, 6-, 7-, 8-hexadecene, 1-, 2-, 3-, 4-, 5-, 6-, 7-, 8-, 9-octadecene, 1-, 2-, 3-, 4-, 5-, 6-, 7-, 8-, 9-, 10-eicosene and 1-, 2-, 3-, 4-, 5-, 6-, 7-, 8-, 9-, 10- and 11-docosene. The sulfonation is followed by hydrolysis and neutralization, after which the olefin sulfonate is present in the mixture as an alkali metal, alkaline earth metal, ammonium, alkyl ammonium, alkanolammonium or glucammonium salt and preferably as a sodium salt. The hydrolyzed α-olefin sulfonation product, i.e. the α-olefin sulfonates, advantageously consists of ca. 60% by weight of alkane sulfonates and ca. 40% by weight of hydroxyalkane sulfonates, of which 80 to 85% by weight are monosulfonates and 15 to 20% by weight disulfonates.

Drying and Granulation

Besides the drying and granulation of neutralized surfactant pastes, it is also possible to subject the acidic sulfonation products to spray neutralization as described, for example, in EP 0 319 819 A1. In this process, the acid and a highly concentrated aqueous sodium hydroxide solution are separately exposed to a gaseous medium, subsequently combined in stoichiometric quantities, neutralized in a multicomponent nozzle and sprayed into the dryers or granulators under a high propellent gas pressure.

Since the sulfation is never complete, above all in industrial installations, conventional alkyl sulfate pastes always contain unsulfonated components. In the case of monoglyceride sulfates, these unsulfonated components are understood to be the unreacted monoglycerides. The aqueous alkyl sulfate pastes normally contain the unsulfonated components in quantities of 0.2 to 10, preferably 0.4 to 5 and more preferably 0.6 to 0.8% by weight, based on the active substance content. Aqueous technical monoglyceride (ether) sulfate pastes contain between 0.6 and 10% by weight of unsulfonated components and 10 to 50, preferably 15 to 45 and more particularly 20 to 35% by weight of technical coconut monoglyceride sulfate sodium salt. The balance of the pastes to 100% by weight is water and salts (0.1 to 20 and preferably 0.5 to 5% by weight, based on the active substance content).

SKET Granulation

A preferred possibility is to subject the water-containing surfactant paste to so-called SKET granulation. SKET granulation is understood to be a simultaneous granulation and drying process preferably carried out in batches or continuously in a fluidized bed. To this end, aqueous pastes of anionic surfactants and the liquid intermediate products are introduced simultaneously or successively into the fluidized bed through one or more nozzles. Preferred fluidized-bed arrangements have base plates measuring 0.4 to 5 m. The SKET granulation is preferably carried out at fluidizing air flow rates of 1 to 8 m/s. The granules are preferably discharged from the fluidized bed via a sizing stage. Sizing may be carried out, for example, by means of a sieve or by an air stream flowing in countercurrent (sizing air) which is controlled in such a way that only particles beyond a certain size are removed from the fluidized bed while smaller particles are retained in the fluidized bed. The inflowing air is normally made up of the heated or unheated sizing air and the heated bottom air. The temperature of the bottom air is between 80 and 400° C. and preferably between 90 and 350° C. A starting material, preferably SKET granules from an earlier test batch, is advantageously introduced at the beginning of the SKET granulation process. The water from the fatty anionic surfactant paste evaporates in the fluidized bed, resulting in the formation of partly dried to fully dried nuclei which are coated with further quantities of anionic surfactant and the liquid intermediate product, granulated and again simultaneously dried. The dried granules contain 1 to 2% by weight of residual water. Reference is made in this connection to the teaching of German patent applications DE 4303211 A1 and DE 4303176 A1 of which the disclosures are hereby specifically included in the present specification.

One advantage of the granules is that they are non-tacky and have high bulk densities of 300 to 1,200 g/l and preferably 500 to 800 g/l.

Commercial Applications

The surfactant granules produced in accordance with the invention are used for the production surface-active compositions. The surface-active compositions in question may be laundry detergents, dishwashing detergents, cleaners, fabric softeners and cosmetic preparations for the cleaning and care of skin and hair. They are preferably used for the production of soaps and oral and dental care preparations.

According to the invention, the surfactant granules produced in accordance with the invention may be used on their own or in combination with the surfactant granules mentioned in quantities of 0.1 to 60, preferably 0.5 to 45 and more particularly 0.6 to 20% by weight—based on the preparations and expressed as solids—in surface-active compositions, preferably soaps and oral and dental care preparations. Preferably 0.1 to 20, more preferably 0.5 to 15 and most preferably 0.6 to 45% by weight of the surfactant granules—as described above—are used in soaps and 0.1 to 20 and more particularly 0.6 to 5% by weight in oral and dental care preparations. The surfactant granules according to the invention and the surfactant granules mentioned are used in a ratio to one another of 20:80 to 80:20, preferably 30:70 to 70:30 and more particularly 40:60 to 60:40 parts by weight.

Laundry/dishwashing Detergents and Cleaners

Besides the granules according to the invention, the laundry/dishwashing detergents and cleaners may contain other typical ingredients such as, for example, anionic surfactants, nonionic surfactants, builders, bleaching agents, bleach activators, detergency boosters, enzymes, enzyme stabilizers, redeposition inhibitors, optical brighteners, soil repellents, foam inhibitors, inorganic salts and dyes and perfumes.

Cosmetic Preparations

The surfactant mixtures according to the invention may be used for the production of cosmetic preparations, for example hair shampoos, hair lotions, foam baths, shower baths, creams, gels, lotions, emulsions, wax/fat compounds, stick preparations or powders. These preparations may also contain mild surfactants, oil components, emulsifiers, superfatting agents, pearlizing waxes, consistency factors, thickeners, polymers, silicone compounds, fats, waxes, stabilizers, biogenic agents, deodorizers, anti-dandruff agents, film formers, swelling agents, UV protection factors, antioxidants, hydrotropes, preservatives, insect repellents, self-tanning agents, solubilizers, perfume oils, dyes, germ inhibitors and the like as further auxiliaries and additives.

The bar soaps, preferably syndet soaps, may contain water-soluble or water-swelling structurants, for example starch, preferably wheat or corn starch, as builders. Other suitable builders are fine-particle, water-insoluble alkali metal aluminium silicates, the use of synthetic crystalline sodium alumosilicates containing bound water, more especially zeolite A, being particularly preferred. Zeolite NaX and mixtures thereof with zeolite NaA may also be used. Suitable zeolites have a calcium binding capacity of 100 to 200 mg CaO/g. NTA and/or EDTA may also be used as liquid builders. Suitable plasticizers are fatty alcohols, fatty acid partial glycerides or wax esters containing 12 to 22 carbon atoms in the fatty components.

Oral and Dental Care Preparations

The surfactant granules according to the invention may be used for the production of oral and dental care preparations.

These preparations may contain abrasives and polishes, flavoring components, chitosans and other typical ingredients for toothpastes as further auxiliaries and additives.

The compositions according to the invention may contain chalk, dicalcium phosphate, sodium bicarbonate, sodium sulfate, insoluble sodium metaphosphate, aluminium silicate, layer silicates, hydrotalcites, calcium pyrophosphate, fine-particle synthetic resins, silicas, aluminium oxide, aluminium oxide trihydrate, talcum, zeolites, magnesium aluminium silicate (Veegum®), calcium sulfate, magnesium carbonate and/or magnesium oxide as abrasives and polishes. The percentage content of the abrasives and polishes may be from 1 to 25% by weight and is preferably from 10 to 20% by weight, based on the final compositions.

Besides the surfactants mentioned, other suitable auxiliaries and additives are flavoring components, for example peppermint oil, spearmint oil, anise oil, Japanese anise oil, caraway oil, eucalyptus oil, fennel oil, cinnamon oil, clove oil, geranium oil, sage oil, pimento oil, thyme oil, marjoram oil, basil oil, citrus oil, gaultheria oil or one or more components of these oils isolated from them or synthetically produced such as, for example, menthol, carvone, anethol, cineol, eugenol, cinnamaldehyde, caryophyllene, geraniol, citronellol, linalool, salvia, thymol, terpinene, terpineol, methyl chavicol and methyl salicylate. Other suitable flavoring agents are, for example, methyl acetate, vanillin, ionone, linalyl acetate, rhodinol and piperitone. Suitable sweetening agents are either natural sugars, such as sucrose, maltose, lactose and fructose, or synthetic sweeteners such as, for example, saccharin sodium salt, sodium cyclamate or aspartame. The flavoring components may make up from 0 to 3% by weight and preferably from 1 to 2% by weight of the final compositions.

Chitosans are biopolymers which belong to the group of hydrocolloids. Chemically, they are partly deacetylated chitins differing in their molecular weights which contain the following—idealized—monomer unit:

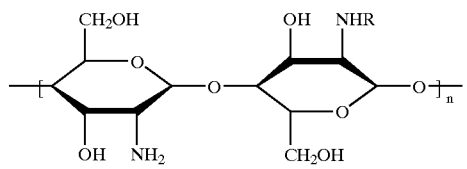

In contrast to most hydrocolloids, which are negatively charged at biological pH values, chitosans are cationic biopolymers under these conditions. The positively charged chitosans are capable of interacting with oppositely charged surfaces and are therefore used in cosmetic hair-care and body-care products and pharmaceutical preparations (cf. Ullmann's Encyclopedia of Industrial Chemistry, 5th Ed., Vol. A6, Weinheim, Verlag Chemie, 1986, pages 231-332). Overviews of this subject have also been published, for example, by B. Gesslein et al. in HAPPI 27, 57 (1990), O. Skaugrud in Drug Cosm. Ind. 148, 24 (1991) and E. Onsoyen et al. in Seifen-Öle-Fefte-Wachse 117, 633 (1991). Chitosans are produced from chitin, preferably from the shell residues of crustaceans which are available in large quantities as inexpensive raw materials. In a process described for the first time by Hackmann et al., the chitin is normally first deproteinized by addition of bases, demineralized by addition of mineral acids and, finally, deacetylated by addition of strong bases, the molecular weights being distributed over a broad spectrum. Corresponding processes are known, for example, from Makromol. Chem. 177, 3589 (1976) or French patent application FR 2701266 A. Preferred types are those which are disclosed in German patent applications DE 4442987 A1 and DE 19537001 A1 (Henkel) and which have an average molecular weight of 800,000 to 1,200,000 dalton, a Brookfield viscosity (1% by weight in glycolic acid) below 5,000 mPas, a degree of deacetylation of 80 to 88% and an ash content of less than 0.3% by weight. Besides the chitosans as typical cationic biopolymers, anionically or nonionically derivatized chitosans such as, for example, the carboxylation, succinylation or alkoxylation products described, for example, in German patent DE 3713099 C2 (L'Oréal) and in German patent application DE 19604180 A1 (Henkel) are also suitable for the purposes of the invention. The percentage content of chitosans may be from 0 to 2% by weight and is preferably from 0.1 to 0.5% by weight, based on the final preparation.

Other suitable auxiliaries and additives, particularly for use in toothpastes, are humectants, for example sorbitol, glycerol or polyethylene glycols; consistency factors; deodorizing agents; swelling agents and binders, for example carboxymethyl cellulose or xanthan gum, agents active against diseases of the mouth and teeth; water-soluble fluorine compounds, for example sodium fluoride or sodium monofluorophosphate.

Basically, the percentage content of these auxiliaries and additives is not critical and depends upon the nature of the ultimate composition. Normally, it is from 5 to 98% by weight and preferably from 80 to 90% by weight, based on the final preparation.

A typical toothpaste—another subject of the present invention—has the following typical composition (water to 100% by weight):

(a) 0.1 to 20, preferably 0.6 to 5% by weight surfactant granules,
(b) 1 to 25, preferably 10 to 20% by weight abrasives and polishes,
(c) 0 to 65, preferably 10 to 45% by weight humectants,
(d) 0 to 2, preferably 0.1 to 0.5% by weight chitosans,
(e) 0 to 3, preferably 1 to 2% by weight flavorings and
(f) 0 to 5, preferably 1 to 3% by weight other auxiliaries, with the proviso that the quantities used add up to 100% by weight.

Examples

In Examples 1 and 2, an acidic sulfuric acid semiester of cocomonoglyceride (CMGSS) was spray-neutralized with 50% by weight sodium hydroxide in a multicomponent nozzle (propellent gas: ammonia) and directly dried and at the same time granulated in a Glatt AGT granulator/dryer in accordance with the teaching of EP 0319819 A1. The starting material used consisted of surfactant granules which had been produced in a preceding batch (under the same process conditions) and which had substantially the same composition as the final granules of Examples 1 and 2. The process conditions are set out in Table 1.

Dust-free non-tacky granules with high surfactant contents were obtained in both Examples (see Table 2). In all Examples, the percentage of granules with a particle size above 2.5 mm was below 5% by weight.

TABLE 1

Process parameters

| Process parameters | 1 | 2 |
|---|---|---|
| Fluidized bed | | |
| diameter in mm | 400 | 400 |
| area in $m^2$ | 0.13 | 0.13 |
| Fluidizing air flow rate in m/s (under working conditions without propellent gas) | 2.35 | 1.92 |
| Temperatures in °C. | | |
| bottom air | 85 | 89 |
| sizing air | 20 | 10 |
| fluidizing air ca. 5 cm above base plate | 62 | 69 |
| air exit | 60 | 60 |
| Throughput | | |
| CMGSS | 30 | 50 |
| NaOH | 7.1 | 12.9 |
| Starting material in kg | 20 | 20 |

TABLE 2

Characteristic data of the products

| Characteristic data of the products | 1 | 2 |
|---|---|---|
| Surfactant content in % by weight (incl. salt and unsulfonateds) | 99 | 94 |
| Water content in % by weight | ≦1 | 6 |
| Bulk density in g/l | 600 | 580 |
| Sieve analysis: | | |
| 2.50 mm | — | — |
| 1.60 mm | 2.5 | 23.4 |
| 0.80 mm | 28.6 | 34.9 |
| 0.60 mm | 25.3 | 14.5 |
| 0.40 mm | 24.7 | 12.7 |
| 0.20 mm | 12.6 | 11.0 |
| 0.10 mm | 6.3 | 3.5 |
| 0.05 mm | — | — |
| ≦0.05 mm | — | — |

The surfactant mixtures were used in a standard toothpaste formulation. Foaming behavior was tested by the friction foam method in an EHMEDA friction foam generator [Fette, Seifen, Anstrichmift. 66, 955 (1964)]. To this end, 20 g toothpaste were dispersed in 180 g water and the resulting dispersion was heated to 45° C. in the foam cylinder. Foam was generated therein by rubbing of a vertically rotating Perlon brush for 60 s at 2600 r.p.m. against a cylindrically shaped metal wire gauze. Table 1 below shows the foam volume 0.5 min after the end of foam generation. Cleaning performance was evaluated after teeth cleaning by 5 independent examiners on the basis of the following criteria: (++)=very good cleaning by abrasives; (+)=good to satisfactory cleaning by abrasives. Examples 1 to 3 in Table 1 correspond to the invention, Examples C1 to C3 are intended for comparison.

TABLE 1

Evaluation of toothpastes (quantities as % by weight)

| Composition/performance | 1 | 2 | 3 | C1 | C2 | C3 |
|---|---|---|---|---|---|---|
| Plantapon ® $CMGS_G$ Cocomonoglyceride sulfate granules | 2 | 1.5 | 1 | – | – | – |
| Plantapon ® CMGS Cocomonoglyceride sulfate paste (25% by weight) | – | – | – | 8 | 8 | 8 |
| Plantacare ® 1200 G Lauryl Glucoside | – | 1.5 | 1.5 | – | – | 1.5 |
| Texapon ® CP-G 95 Lauryl Sulfate | – | – | 1.5 | – | – | 1.5 |
| Chitosan | – | 0.1 | 0.1 | – | – | 0.1 |
| Glycerin (86% by weight) | 25 | 25 | 25 | 25 | 25 | 25 |
| Keltrol ® F Xanthan gum | 1.3 | 0.8 | 1.3 | 1.3 | 0.8 | 1.3 |
| Polyethylene glycol (mol. wt. 400) | 2 | 1.5 | – | 2 | 2 | – |
| Sorbitol (70% by wt.) | 15 | 15 | 15 | 15 | 15 | 15 |
| Sident ® 12 DS Precipitated silica | 15 | 15 | 15 | 15 | 22 | 15 |
| Sodium fluoride | 0.2 | 0.2 | 0.2 | 0.2 | 0.2 | 0.2 |
| Sodium saccharin | 0.2 | 0.2 | 0.2 | 0.2 | 0.2 | 0.2 |
| Flavors | 1 | 1 | 1 | 1 | 1 | 1 |
| Dyes | 1 | 1 | 1 | 1 | 1 | 1 |
| Water | to 100 | | | | | |
| Wilsmann friction foam [ml] | 790 | 840 | 830 | 770 | 790 | 840 |
| Cleaning performance | ++ | ++ | ++ | + | ++ | + |

Bar soaps were pressed on the basis of formulations 1 to 3 according to the invention and comparison formulations C1 and C2 and tested for their performance properties (evaluation on a scale of –=satisfactory, ++=good and +++= very good). The results are set out in Table 2. According to all the test criteria, the formulation according to the invention shows distinct advantages. Thus, bar soaps containing monoglyceride (ether) sulfate granules are distinguished from Comparison Examples 1 and 2 by a lesser tendency to take up water, i.e. to become soft, greater stability and better foaming.

TABLE 2

Bar soaps - compositions and properties (quantities as % by weight)

| Composition/performance | 1 | 2 | 3 | C1 | C2 |
|---|---|---|---|---|---|
| Plantapon ® $CMGS_G$ Cocomonoglyceride sulfate granules | 9 | 9 | 9 | – | – |
| Plantapon ® CGMS Cocomonoglyceride sulfate paste (25%) | – | – | – | 4 | 9 |
| Witconate ® A06 Sodium C12/14 Olefin Sulfonate | 30 | – | 30 | 35 | – |
| Texin ® 128 P Disodium Lauryl Sulfosuccinate | – | 30 | – | – | 35 |
| Plantacare ® APG 1200 G Lauryl Glucoside | – | 15 | 15 | 15 | 10 |
| Hydrenol ® DV Cetylstearyl Alcohol | 12 | 12 | 12 | 12 | 12 |
| Paraffin Oil (Mp. 54–56° C.) | 8 | 8 | 8 | 8 | 8 |
| C-Plus 05085 Maize starch, degraded | 8 | 8 | 8 | 8 | 8 |
| Cutina FS 45 Palmitic Acid (and) Stearic Acid | 5.5 | 5.5 | 5.5 | 5.5 | 5.5 |
| Cutina GMS-V Glyceryl Stearate | 2 | 2 | 2 | 2 | 2 |
| Novata BD Coco Glyceride | 2 | 2 | 2 | 2 | 2 |
| Sorbitol/Karion F | 2 | 2 | 2 | 2 | 2 |
| Merquat 550 Polyquaternium-7 | 1 | 1 | 1 | 1 | 1 |
| Perfume Oil Polyquaternium-7 | 1 | 1 | 1 | 1 | 1 |

TABLE 2-continued

Bar soaps - compositions and properties (quantities as % by weight)

| Composition/performance | 1 | 2 | 3 | C1 | C2 |
|---|---|---|---|---|---|
| Bayertitan AZ Titanium Dioxide | 0.5 | 0.5 | 0.5 | 0.5 | 0.5 |
| Tendency to take up water | + | − | − | ++ | ++ |
| Stability | + | ++ | ++ | − | + |
| Friction foam | ++ | +++ | ++ | + | + |

What is claimed is:

1. An aqueous oral and dental care composition comprising: (a) from about 0.1 to about 20% by weight of surfactant granules which are the product of the process which comprises subjecting an aqueous paste comprised of from about 40 to about 60% by weight of a monoglyceride (ether) sulfate to simultaneous drying and granulation in a fluidized bed; (b) from about 1 to about 25% by weight of an abrasive, a polish, or a combination thereof; (c) from 0 to about 65% by weight of a humectant; (d) from 0 to about 2% by weight of chitosan; (e) from 0 to about 3% by weight of a flavoring and; (f) from 0 to about 5% by weight other auxiliaries including water wherein the weight of all components adds up to 100% by weight.

2. The composition of claim 1 wherein the monoglyceride (ether) sulfate is a compound of the formula (I):

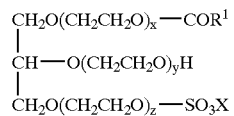

wherein $R^1CO$ is a linear or branched acyl group having from about 6 to about 22 carbon atoms; x+y+z=0 to 30 and X is an alkali metal or alkaline earth metal.

3. The composition of claim 2 wherein $R^1CO$ is a linear acyl group having from about 12 to about 14 carbon atoms; x+y+z=0 and X is sodium.

4. The composition of claim 1 wherein component (a) is further comprised of additional surfactant granules containing a fatty alcohol sulfate, a sulfosuccinate, an olefin sulfonate, and an alkyl and/or alkenyl oligoglycoside.

5. The composition of claim 4 wherein the weight ratio of the additional surfactants to the monoglyceride (ether) sulfate is from about 20:80 to about 80:20.

6. An aqueous oral and dental care composition comprising: (a) from about 0.6 to about 5% by weight of surfactant granules which are the product of the process which comprises subjecting an aqueous paste comprised of from about 40 to about 60% by weight of a monoglyceride (ether) sulfate to simultaneous drying and granulation in a fluidized bed; (b) from about 10 to about 20% by weight of an abrasive, a polish, or a combination thereof; (c) from 10 to about 45% by weight of a humectant; (d) from 0.1 to about 0.5% by weight of chitosan; (e) from 1 to about 2% by weight of a flavoring and; (f) from 1 to about 3% by weight other auxiliaries including water wherein the weight of all components adds up to 100% by weight.

* * * * *